US011439648B2

(12) United States Patent
Shelach et al.

(10) Patent No.: US 11,439,648 B2
(45) Date of Patent: Sep. 13, 2022

(54) USE OF TOPICAL BRAF INHIBITOR COMPOSITIONS FOR TREATMENT OF RADIATION DERMATITIS

(71) Applicant: Lutris Pharma Ltd., Tel Aviv (IL)

(72) Inventors: Noa Shelach, Tel Aviv (IL); Noa Lowenton-Spier, Tel Aviv (IL)

(73) Assignee: Lutris Pharma Ltd., Tel Aviv (IL)

( * ) Notice: Subject to any disclaimer, the term of this patent is extended or adjusted under 35 U.S.C. 154(b) by 0 days.

(21) Appl. No.: 17/384,221

(22) Filed: Jul. 23, 2021

(65) Prior Publication Data

US 2021/0346389 A1 Nov. 11, 2021

Related U.S. Application Data

(63) Continuation of application No. PCT/IB2020/051073, filed on Feb. 11, 2020.

(60) Provisional application No. 62/804,235, filed on Feb. 12, 2019.

(51) Int. Cl.
| | | |
|---|---|---|
| *A61K 31/52* | (2006.01) | |
| *A61K 31/167* | (2006.01) | |
| *A61K 31/4184* | (2006.01) | |
| *A61K 31/437* | (2006.01) | |
| *A61K 31/44* | (2006.01) | |
| *A61K 31/4439* | (2006.01) | |
| *A61K 31/506* | (2006.01) | |
| *A61K 31/517* | (2006.01) | |
| *A61K 31/675* | (2006.01) | |

(52) U.S. Cl.
CPC ............ *A61K 31/52* (2013.01); *A61K 31/167* (2013.01); *A61K 31/4184* (2013.01); *A61K 31/437* (2013.01); *A61K 31/44* (2013.01); *A61K 31/4439* (2013.01); *A61K 31/506* (2013.01); *A61K 31/517* (2013.01); *A61K 31/675* (2013.01)

(58) Field of Classification Search
None
See application file for complete search history.

(56) References Cited

U.S. PATENT DOCUMENTS

| | | | |
|---|---|---|---|
| 5,753,612 A | 5/1998 | Mitrani | |
| 7,989,461 B2 | 8/2011 | De Morin et al. | |
| 8,440,674 B2 | 5/2013 | De Morin et al. | |
| 8,557,830 B2 | 10/2013 | Smith et al. | |
| 9,388,165 B2 | 7/2016 | Bae et al. | |
| 10,632,123 B2* | 4/2020 | Shelach | A61K 31/404 |
| 10,927,112 B2* | 2/2021 | Shelach | C07D 401/10 |
| 11,197,861 B2* | 12/2021 | Shelach | A61K 31/517 |
| 11,339,163 B2* | 5/2022 | Shelach | C07D 401/14 |
| 2011/0118245 A1 | 5/2011 | Abraham et al. | |
| 2013/0190286 A1 | 7/2013 | Steurer et al. | |
| 2013/0226549 A1 | 8/2013 | Tseng et al. | |
| 2014/0005198 A1 | 1/2014 | Smith et al. | |
| 2017/0100345 A1 | 4/2017 | Ribas et al. | |
| 2018/0369247 A1 | 12/2018 | Shelach | |
| 2020/0163967 A1* | 5/2020 | Rosen | A61K 31/4439 |
| 2021/0070757 A1* | 3/2021 | Shelach | C07D 401/10 |

FOREIGN PATENT DOCUMENTS

WO 2015/171833 A1 11/2015

OTHER PUBLICATIONS

Hecht et al., "Radiosensitization by BRAF inhibitor therapy—mechanism and frequency of toxicity in melanoma patients", 2015, Annals of Oncology, 26(6), pp. 1238-1244. (doi.org/10.1093/annonc/mdv139) (Year: 2015).*
International Search Report from International Application No. PCT/IB2020/051073 dated Mar. 30, 2020.
Anker et al., "Avoiding Severe Toxicity from Combined BRAF Inhibitor and Radiation Treatment: Consensus Guideline from the Eastern Cooperative Oncology Group (ECOG)", Int J Radiat Oncol Biol Phys, Nov. 9, 2016.
Ocvirk et al., "A review of the treatment options for skin rash induced by EGFR-targeted therapies: evidence from randomized clinical trials and a metaanalysis", Radiology and Oncology, 47(2), pp. 166-175, 2013.
Manousaridis et al., "Cutaneous side effects of inhibitors of the RAS/RAF/MEK/ERK signaling pathway and their management", Journal of the European Academy of Dermatology and Venereology, 27(1), pp. 11-18, 2013.
Gencler et al., "Cutaneous Side Effects of BRAF Inhibitors in Advanced Melanoma: Review of the Literature", Dermatology Research and Practice, 2016.
Carnahan et al., "Selective and potent RAF inhibitors paradoxically stimulate normal cell proliferation and tumor growth", Mol Cancer Ther. Aug. 2020;9(8): 2399-410.
Gibney et al., "Paradoxical oncogenesis and the long-term consequences of BRAF inhibition in melanoma", Nat Rev Clin Oncol, Jul. 2013; 10(7):390-9.
Hatzivassiliou et al., "RAF inhibitors prime wild-type RAF to activate teh MAPK pathway and enhance growth", Nature 2010, vol. 464, pp. 431-436.
Holcmann et al., "Mechanisims underlying skin disorders induced by EGFR inhibitors", Mol Cell Oncol. Jun. 1, 2015:2(4).
Smith et al., "Selective Inhibitors of the Mutant B-Raf Pathway: Discovery of a Potent and Orally Bioavailable Aminoisoquinoline", J. Med. Chem. 2009, 52, 6189-6192.

\* cited by examiner

*Primary Examiner* — My-Chau T. Tran
(74) *Attorney, Agent, or Firm* — Greenberg Traurig, LLP (57) ABSTRACT

The present invention discloses methods of treatment, prevention and/or amelioration of radiation dermatitis caused by radiotherapy, by administration to a subject in need thereof of a topical composition comprising a therapeutically or prophylactically effective amount of at least one BRaf inhibitor of this invention, thus treating, preventing and/or ameliorating the effects of radiation dermatitis.

18 Claims, 1 Drawing Sheet

USE OF TOPICAL BRAF INHIBITOR COMPOSITIONS FOR TREATMENT OF RADIATION DERMATITIS

CROSS REFERENCE TO RELATED APPLICATIONS

This application is a continuation of PCT/IB2020/051073, filed Feb. 11, 2021, which claims priority to U.S. Provisional Patent Application Ser. No. 62/804,235, filed on Feb. 12, 2019, the entire contents of each of which are hereby incorporated by reference in their entireties.

FIELD OF THE INVENTION

The present invention relates to methods of treatment of radiation dermatitis, by administration to a subject in need thereof a composition comprising a therapeutically and/or prophylactically effective amount of at least one BRaf inhibitor or a combination thereof and a pharmaceutically acceptable carrier or excipient.

BACKGROUND

Radiation therapy (RT) remains an essential component of cancer treatment, with nearly 50% of cancer patients receiving RT at some point during the course of their illness. Of those receiving RT, as many as 95% may experience some form of radiation dermatitis, or radiation-induced skin injury. Radiation dermatitis can manifest as acute erythema and desquamation, or as chronic effects including skin atrophy, telangiectasias, and fibrosis. These skin changes result from a combination of RT features and intrinsic patient risk factors. While a reduced total dose of radiation and use of an advanced mode of radiation delivery may help to mitigate the severity of radiation effects on the skin, radiation dermatitis remains one of the most common side effects of RT. This condition can affect a patient's quality of life both during and after treatment. If severe, it carries the risk of limiting the dose of radiation or interrupting the treatment schedule, which could negatively impact treatment efficacy. Consequently, managing radiation-induced skin injury during and after treatment is an important aspect of cancer care. Despite technological advances in radiation delivery and growing interest in managing skin reactions, there is no gold standard in the management of radiation dermatitis.

Radiation dermatitis may be a side-effect of radiotherapy, for some benign conditions.

There is an unmet need in the art for the development of novel methods of prophylaxis and treatment, to help alleviate the radiation dermatitis caused by radiation during the course of treatment and after the radiation has terminated.

BRaf is a protein kinase involved in the regulation of the mitogen activated protein kinase (MAPK) signaling pathway and cell proliferation. Mutations in BRaf can induce constitutive signaling through the MAPK pathway which may result in uncontrolled cell proliferation and malignancy.

Use of BRaf inhibitors has been demonstrated to be associated with inhibition of MAPK signaling, as can be determined by inhibition or reduction in level of phosphorylated ERK, which is the downstream effector of BRaf Yet, it has been further observed that paradoxically, BRaf inhibitors can induce an opposite effect of activation of MAPK signaling in BRAF wild-type cells and induce cell proliferation. (N. Shelach, U.S. Patent Application No. 20180369247).

SUMMARY OF THE INVENTION

The present disclosure provides methods of treatment of radiation dermatitis by administration to a subject in need thereof a composition comprising a topical prophylactically and/or therapeutically effective amount of at least one BRaf inhibitor of Groups A-D as defined herein. The present disclosure also provides compositions comprising the BRaf inhibitors of Groups A-D and methods of treating dermatological adverse reactions induced by radiation therapy using the topical BRaf inhibitors and compositions of the present disclosure.

DETAILED DESCRIPTION OF THE INVENTION

Provided herein are methods of treating radiation dermatitis using the topical BRaf inhibitors and compositions of the present disclosure.

Radiation dermatitis, also known as radiodermatitis, X-ray dermatitis, radiation skin damage or radiation burn, is a side-effect of radiotherapy, mostly used for cancer treatment. Its symptoms include redness, itching, flaking, peeling, soreness, blistering, fibrosis, scarring and skin ulcers. These are serious symptoms, which may negatively impact the patient's willingness to continue treatment and his/her quality of life.

The radiation dermatitis lasts after the course of the radiotherapy has been completed and therefore, the treatment needs to be continued thereafter.

There are several known methods of treatment of radiation dermatitis: skin emollients, corticosteroids, water-based dressing, injectable amifostine and silver-based dressings/ointments and antibiotics for secondary skin infections. Of the above known methods of treatment, amifostine is probably the most effective, but the injectable way of administration is a drawback.

It occurred to the inventors that topical BRaf inhibitors may be used for the treatment of radiation dermatitis, based on mechanistic arguments of the well-known paradoxical effect.

N. Shelach showed in a co-pending patent application PCT/IL2017/050301 titled "Use of BRaf Inhibitors for Treating Cutaneous Reactions" that this paradoxical activation of MAPK can be used for treating cutaneous adverse reactions induced by treatment with EGFR or PI3K inhibitors.

Without wishing to be bound by theory, the inventors theorize that a different aspect of the same mechanism may serve for the treatment of radiation dermatitis with topical BRaf inhibitors. This is probably due to the BRaf inhibitors' positive impact of the cell proliferation (see Example 1).

The use of BRaf inhibitors in BRaf mutated cells has been demonstrated to be associated with the inhibition of cell proliferation, which is the downstream effector of BRaf and MAPK.

Yet, it has been observed that BRaf inhibitors can paradoxically induce an opposite effect of activating MAPK signaling and inducing cell proliferation in BRaf wild-type cells. The underlying mechanisms of paradoxical MAPK activation have been attributed to dimerization of wild-type BRaf and c-Raf and transactivation of the non-inhibited Raf protein leading to subsequent MAPK pathway activation and cell proliferation.

Carnahan J. et al. (Mol. Cancer Ther. 9(8) August 2010) demonstrated that selective and potent Raf inhibitors can paradoxically stimulate normal cell proliferation. A series of orally bioavailable kinase inhibitors disclosed by Smith A. L. et al., J. Med. Chem. 2009, 52, 6189-6192 showed potent biochemical activity. For example, Compound 1 of the series (C-1) showed significant potency ($^{WT}$B-Raf Ki=1 nmol/L, V600EB-Raf Ki=1 nmol/L, and C-Raf Ki=0.3 nmol/L).

Carnahan et el. found that in cells with wild-type B-Raf and mutated K-ras, exposure to Raf inhibitors resulted in a dose-dependent and sustained paradoxical activation of mitogen-activated protein kinase (MAPK) signaling. BRaf inhibition led to entry into the cell cycle and enhanced proliferation.

In some embodiments, there is provided a method of treatment, prevention or alleviation of radiation dermatitis by administration to a subject in need thereof a topical composition comprising a therapeutically and/or prophylactically effective amount of at least one BRaf inhibitor or a combination thereof and a pharmaceutically acceptable carrier or excipient.

The at least one BRaf inhibitor(s) used in the composition of this invention belong to several structural and functional Groups A-D.

A. Commercially available BRaf inhibitors, selected from BAY43-9006 (Sorafenib), LGX818 (encorafenib), PLX4032 (vemurafenib), GSK2118436 (dabrafenib), ARQ736, ARQ680, AZ628, C-1, C-15, C-19, C-A, CEP-32496, GDC-0879, NMS-P186, NMS-P349, NMS-P383, NMS-P396, NMS-P730, PLX3603 (RO5212054), PLX4720 (Difluorophenyl-sulfonamine), PF-04880594, PLX4734, RAF265, RO4987655, SB590885, ZM336372, BMS908662, WYE-130600, TAK632, MLN 2480, XL281.

C-1, C-15, C-19, C-A, C-A and ZM336372 are disclosed, for example, in Carnahan et. al. (Mol. Cancer Ther. 2010 August; 9(8):2399-410) and Smith et. al. (J. Med. Chem., 2009, 52 (20), pp 6189-619), and comprise the following molecules structures:

C-1

C-15

C-19

C-A

ZM336372 (ZM)

B. BRaf inhibitors of formula (I):

wherein R is selected from the group consisting of p-chlorophenyl, 3-ethynylphenyl, 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, 3,5-dihydroxyphenyl, phenyl-3-sulfonamide or 3-(trifluoromethyl)phenyl, or a pharmaceutically acceptable salt or a solvate thereof;

C. BRaf inhibitors of formula (II):

wherein R is NHR1, wherein R1 is 2-fluoro-4-iodophenyl, or a pharmaceutically acceptable salt or a solvate thereof;

D. BRaf inhibitors of formula (III):

wherein R is NHR1, wherein R1 is 3-ethynylphenyl, 3-chloro-4-fluorophenyl, 2-fluoro-4-iodophenyl, or 4-chloro-3-(trifluoromethyl) phenyl, or a pharmaceutically acceptable salt or a solvate thereof;

or a combination thereof; and a pharmaceutically acceptable carrier or excipient.

An outstanding BRaf inhibitor is the compound of formula (I), wherein R is 3-(trifluoromethoxy)phenyl.

The compounds of formulae (I), (II) and (III) were disclosed in International Publication No. WO2019/026065, Shelach N.

In some embodiments, the compounds of present disclosure increase cell proliferation.

Compositions

In some embodiments, provided herein is a pharmaceutical composition comprising at least one BRaf inhibitor of above Groups A-D.

In some other embodiments, the above pharmaceutical composition may comprise from about 0.1% w/w to about 1% w/w of at least one BRaf inhibitor of groups A-D or a pharmaceutically acceptable salt or a solvate thereof, or a combination thereof, based on the total weight of the composition. For example, the pharmaceutical composition may comprise about 0.1%, 0.2%, 0.3%, 0.4%, 0.5%, 0.6%, 0.7%, 0.8%, 0.9% or 1% w/w, including values and ranges therebetween, of the total weight of the composition of at least one of the BRaf inhibitors of Groups A-D disclosed herein.

In some embodiments, the pharmaceutical composition may comprise from about 0.1% to about 0.2%, from about 0.1% to about 0.3%, from about 0.1% to about 0.4%, from about 0.1% to about 0.5%, from about 0.1% to about 0.6%, from about 0.1% to about 0.7%, from about 0.1% to about 0.8%, from about 0.2% to about 0.9%, from about 0.2% to about 1%, from about 0.25% to about 0.5%, from about 0.25% to about 0.7%, from about 0.25% to about 0.8%, from about 0.5% to about 0.75% or from about 0.5% to about 1% w/w, including values and ranges therebetween, based on the total weight of the composition of any of the BRaf inhibitors disclosed herein.

In some other embodiments, the above pharmaceutical composition may comprise from about 1% w/w to about 5% w/w of at least one BRaf inhibitor of Groups A-D or a pharmaceutically acceptable salt or a solvate thereof, or a combination thereof, based on the total weight of the composition. For example, the pharmaceutical composition may comprise about 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% w/w, including values and ranges therebetween, of any of the BRaf inhibitors of Groups A-D disclosed herein.

In some embodiments, the pharmaceutical composition may comprise from about 1% to about 3%, from about 1% to about 4%, from about 1.5% to about 5%, from about 1.5% to about 4.5%, from about 1.5% to about 3.5%, from about 1.5% to about 3%, from about 2% to about 5%, from about 2% to about 4.5%, from about 2% to about 4%, from about 2.5% to about 5%, from about 2.5% to about 4.5%, from about 2.5% to about 4%, from about 3% to about 5%, from about 3.5% to about 5% w/w, including values and ranges therebetween, based on the total weight of the composition of any of the BRaf inhibitors disclosed herein.

In some other embodiments, a pharmaceutical composition may comprise about 5% w/w to about 10% w/w of a BRaf inhibitor of Groups A-D or a pharmaceutically acceptable salt or a solvate thereof, or a combination thereof, based on the total weight of the composition. For example, the pharmaceutical composition may comprise about 5%, 5.1%, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 7.1%, 7.2%, 7.3%, 7.4%, 7.5%, 7.6%, 7.7%, 7.8%, 7.9%, 8%, 8.1%, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9%, or 10% w/w, including values and ranges therebetween, of any of the BRaf inhibitors of Groups A-D disclosed herein.

In some other embodiments, the pharmaceutical composition may comprise from about 5% to about 9%, from about 5% to about 8.5%, from about 5% to about 8%, from about 5% to about 7.5%, from about 5% to about 7%, from about 6% to about 10%, from about 6% to about 9%, from about 6% to about 8.5%, from about 6% to about 8%, from about 7% to about 10%, from about 7% to about 9.5%, from about 7% to about 8.5%, from about 7.5% to about 10%, from about 8% to about 10% w/w, including values and ranges therebetween, of the total weight of the composition of any of the BRaf inhibitors disclosed herein.

In some other embodiments, the pharmaceutical composition may comprise from about 1% to about 10%, from about 1% to about 8%, from about 1% to about 7%, from about 2% to about 8%, from about 2% to about 7%, from about 2% to about 6%, from about 2.5% to about 7.5%, from about 2.5% to about 5.5%, from about 3% to about 8%, from about 3% to about 7%, from about 4% to about 8%, from about 4% to about 7%, about 4.5% to about 7.5%, from about 4.5% to about 7%, or from about 4.5% to about 6.5% w/w, including values and ranges therebetween, of the total eight of the composition of any of the BRaf inhibitors disclosed herein.

In some embodiments, the pharmaceutical composition comprising any one of the compounds disclosed herein is formulated for topical administration. Topical administration comprises local application of the composition to the skin area of the subject, affected by the radiation dermatitis or to be treated by radiotherapy.

In some embodiments, provided herein is a topical pharmaceutical composition comprising at least one BRaf inhibitor of Groups A-D or a pharmaceutically acceptable salt or a solvate thereof, or a combination thereof, and a pharmaceutically acceptable carrier or excipient. Compositions for topical administration (topical compositions) can be in the form of a gel, a hydrogel, an ointment, a cream, a paste, a foam, a spray, a lotion, a liquid, or a dermal patch and may comprise any of the disclosed compound(s) in any of the amounts described herein.

In some embodiments, a topical pharmaceutical composition comprises a BRaf inhibitor (code name LUT014) of formula:

LUT014 in any of the amounts disclosed herein and a pharmaceutically acceptable carrier or excipient.

In some embodiments, provided herein is a topical pharmaceutical composition comprising LUT014 in any of the w/w % amounts disclosed herein and a pharmaceutically acceptable carrier or excipient. The topical composition comprising LUT014 may be formulated in a dosage form selected from ointment, cream, paste, gel, hydrogel, foam, spray, lotion, liquid and dermal patch.

Another topical dosage form is a paste. Pastes are stiff semi-solid topical dosage forms, containing a high proportion of finely powdered solid such as starch, zinc oxide, calcium carbonate and talc. Another component of pastes is a base, which may be a hydrocarbon, an absorption ingredient, a water-miscible ingredient or a water-soluble ingredient. Pastes are less greasy than ointments.

Topical compositions useful in the present disclosure may be formulated as a solution. Such compositions may comprise an emollient preferably containing from about 1% to about 50% of an emollient(s). As used herein, the term "emollient" refers to materials used for the prevention or relief of dryness, as well as for the protection of the skin. A number of suitable emollients are known and may be used in the present disclosure. For example, Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in the present disclosure may be formulated as emulsions. If the carrier for a topical composition is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, in McCutcheon's Detergents and Emulsifiers, North American Edition, pp. 317-324 (1986), and the ICI Handbook, pp. 1673-1686.

Lotions and creams can be formulated as emulsions. Such lotions and creams may comprise from 0.5% to about 5% of an emulsifier(s). Creams may comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

The topical compositions of this disclosure can also be formulated as a gel (e.g., an aqueous, alcohol, alcohol/water, or oil gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils include, but are not limited to, hydrogenated butylene/ethylene/styrene copolymer and hydrogenated ethylene/propylene/styrene copolymer. Gel compositions may comprise between about 0.1% and 5%, by weight, of such gelling agents.

In addition to the above carriers and excipients, other emollients and surface active agents can be incorporated into the topical compositions, including glycerol trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerin, sorbitol and the like.

Methods

Provided herein are methods of treating, preventing, and/or ameliorating the side-effects of radiotherapy, known as radiation dermatitis.

In some embodiments, the radiation dermatitis is a dermatological or cutaneous adverse reaction induced by radiotherapy.

In some embodiments, provided herein is a method for treating, ameliorating, and/or preventing radiation dermatitis caused by radiation therapy in a subject in need thereof, comprising administering a therapeutically and/or prophylactically effective amount of a composition comprising at least one BRaf inhibitor of Groups A-D and a pharmaceutically acceptable carrier or excipient.

In some embodiments, provided herein are methods for treating, ameliorating, and/or preventing radiation dermatitis caused by radiation therapy in a subject in need thereof, comprising administering a therapeutically and/or prophylactically effective amount of a composition comprising at least one BRaf inhibitor of Group A and a pharmaceutically acceptable carrier or excipient.

In some embodiments, provided herein are methods for treating, ameliorating, and/or preventing radiation dermatitis caused by radiation therapy in a subject in need thereof, comprising administering a therapeutically and/or prophylactically effective amount of a composition comprising at least one BRaf inhibitor of Group B and a pharmaceutically acceptable carrier or excipient.

In some embodiments, provided herein are methods for treating, ameliorating, and/or preventing radiation dermatitis caused by radiation therapy in a subject in need thereof, comprising administering a therapeutically and/or prophylactically effective amount of a composition comprising at least one BRaf inhibitor of Group B (formula (I), wherein R is 3-(trifluoromethoxy)phenyl, code name LUT014) in any of the w/w % amounts disclosed herein and a pharmaceutically acceptable carrier or excipient.

LUT014

In some embodiments, provided herein are methods for treating, ameliorating, and/or preventing radiation dermatitis caused by radiation therapy in a subject in need thereof, comprising administering a therapeutically and/or prophylactically effective amount of a composition comprising at least one BRaf inhibitor of Group C and a pharmaceutically acceptable carrier or excipient.

In some embodiments, provided herein are methods for treating, ameliorating, and/or preventing radiation dermatitis caused by radiation therapy in a subject in need thereof, comprising administering a therapeutically and/or prophylactically effective amount of a composition comprising at least one BRaf inhibitor of Group D and a pharmaceutically acceptable carrier or excipient.

In some embodiments, the subject is a mammal such as a human, dog, and/or cat.

In some embodiments, methods disclosed herein comprise topical administration of a therapeutically and/or prophylactically effective amount of the compounds/compositions of the present disclosure.

In some embodiments, methods disclosed herein comprise topically administering about 0.1 mg/day to about 1 mg/day of one or more compounds of the present disclosure.

In some embodiments, methods disclosed herein comprise topically administering about 0.1 mg/day, about 0.2 mg/day, about 0.3 mg/day, about 0.4 mg/day, about 0.5 mg/day, about 0.6 mg/day, about 0.7 mg/day, about 0.8 mg/day, about 0.9 mg/day, or about 1 mg/day, including values and ranges therebetween, of one or more compounds of the present disclosure. In some embodiments, methods disclosed herein comprise topically administering about 0.1 mg/day to about 0.5 mg/day, about 0.2 mg/day to about 0.8 mg/day, about 0.2 mg/day to about 0.5 mg/day, or about 0.5 mg/day to about 1 mg/day, including values and ranges therebetween, of one or more compounds of the present disclosure.

In some embodiments, methods disclosed herein comprise topically administering about 1 mg/day to about 5 mg/day of one or more compounds of the present disclosure. In some embodiments, methods disclosed herein comprise topically administering about 1 mg/day, 1.5 mg/day, 2 mg/day, 2.5 mg/day, 3 mg/day, 3.5 mg/day, 4 mg/day, 4.5 mg/day, or 5 mg/day, including values and ranges therebetween, of one or more compounds of the present disclosure.

In some embodiments, methods disclosed herein comprise topically administering about 5 mg/day to about 10 mg/day of one or more compounds of the present disclosure. In some embodiments, methods disclosed herein comprise topically administering about 5 mg/day, about 5.5 mg/day, about 6 mg/day, about 6.5 mg/day, about 7 mg/day, about 7.5 mg/day, about 8 mg/day, about 8.5 mg/day, about 9 mg/day, about 9.5 mg/day, or about 10 mg/day, including values and ranges therebetween, of one or more compounds of the present disclosure.

In some embodiments, methods disclosed herein comprise topically administering about 1 mg/day to about 10 mg/day, about 1 mg/day to about 8 mg/day, about 2 mg/day to about 8 mg/day, about 2.5 mg/day to about 7.5 mg/day, about 3 mg/day to about 8 mg/day, about 3 mg/day to about 6 mg/day, or about 4 mg/day to about 8 mg/day, including values and ranges therebetween, of one or more compounds of the present disclosure.

In some embodiments, the amount of the compound administered depends on the nature of the compound, the mode of administration, and/or the severity of the cutaneous reaction. The prophylactically and/or therapeutically effective amount that need to be administered to a patient can be determined by dose-ranging clinical studies known in the art.

In some embodiments, the methods disclosed herein reduce the severity of the radiation dermatitis reactions.

The most commonly used systems to grade the severity of cutaneous adverse reactions are the Radiation Therapy Oncology Group (RTOG) grading scale and the National Cancer Institute's Common Terminology Criteria for Adverse Events (CTCAE) version 5.0, which recognizes 6 grades shown below.

Dermatitis radiation: (reproduced from page 72 of the CTCEA version 5):
Grade 0—No change
Grade 1—Faint erythema or dry desquamation
Grade 2—Moderate to brisk erythema; patchy moist desquamation; mostly confined to skin folds and creases; moderate edema.
Grade 3—Moist desquamation in areas other than skin folds and creases; bleeding induced by minor trauma or abrasion.
Grade 4—Life-threatening consequences; skin necrosis or ulceration of full thickness dermis; spontaneous bleeding from involved site; skin graft indicated.
Grade 5—Death RTOG grading scale for radiation dermatitis:
Grade 0—No change
Grade 1—Faint erythema; dry desquamation; epilation; decreased sweating
Grade 2—Tender or bright erythema; moderate edema; patchy moist desquamation
Grade 3—Moist desquamation in areas other than skin folds; pitting edema
Grade 4—Ulceration; hemorrhage; necrosis
Grade 5—Death In some embodiments, the methods disclosed herein reduce the severity of the cutaneous adverse reactions from grade 4 to grade 3, 2, 1, or 0, as defined by National Cancer Institute Common Terminology Criteria for Adverse Events (NCI-CTCAE) version 5.0 or according to the Radiation Therapy Oncology Group (RTOG) grading scale.

In some embodiments, the methods disclosed herein reduce the severity of the cutaneous adverse reactions from grade 3 to grade 2, 1, or 0, as defined by NCI-CTCAE version 5.0 or according to the Radiation Therapy Oncology Group (RTOG) grading scale.

In some embodiments, the methods disclosed herein reduce the severity of the cutaneous adverse reactions from grade 2 to grade 1 or 0, as defined by NCI-CTCAE version 5.0 or according to the Radiation Therapy Oncology Group (RTOG) grading scale.

In some embodiments, the methods disclosed herein reduce the severity of the cutaneous adverse reactions from grade 1 to grade 0, as defined by NCI-CTCAE version 5.0 or according to the Radiation Therapy Oncology Group (RTOG) grading scale.

In some embodiments, the methods disclosed herein prevent, partially or completely, the development of cutaneous adverse reactions.

In some embodiments, the methods disclosed herein prevent, partially or completely, the development of grade 4, grade 3, grade 2, or grade 1 of the cutaneous adverse reactions, as defined by NCI-CTCAE version 5.0 or according to the Radiation Therapy Oncology Group (RTOG) grading scale.

In some embodiments, the methods disclosed herein prevent the escalation of the cutaneous adverse reaction. For example, in some embodiments, the methods disclosed herein prevent the escalation of the cutaneous adverse reaction from grade 0 to grade 1, 2, 3, or 4, as defined by NCI-CTCAE version 5.0 or according to the Radiation Therapy Oncology Group (RTOG) grading scale.

In another embodiment, the methods disclosed herein prevent the escalation of the cutaneous adverse reaction from grade 1 to grade 2, 3, or 4, as defined by NCI-CTCAE version 5.0 or according to the Radiation Therapy Oncology Group (RTOG) grading scale.

In another embodiment, the methods disclosed herein prevent the escalation of the cutaneous adverse reaction from grade 2 to grade 3 or 4, as defined by NCI-CTCAE version 5.0 or according to the Radiation Therapy Oncology Group (RTOG) grading scale.

In another embodiment, the methods disclosed herein prevent the escalation of the cutaneous adverse reaction from grade 3 to grade 4, as defined by NCI-CTCAE version 5.0 or according to the Radiation Therapy Oncology Group (RTOG) grading scale.

In some embodiments, there is provided the use of a topical composition comprising a therapeutically and/or prophylactically effective dose of at least one BRaf inhibitor or a combination thereof and a pharmaceutically acceptable carrier or excipient for the treatment, prevention or alleviation of radiation dermatitis by topical administration to a subject in need thereof.

In some embodiments, there is provided the above use, wherein said composition comprises a therapeutically and/or prophylactically effective dose of at least one BRaf inhibitor selected from BAY43-9006 (Sorafenib), LGX818 (encorafenib), PLX4032 (vemurafenib), GSK2118436 (dabrafenib), ARQ736, ARQ680, AZ628, C-1, C-15, C-19, C-A, CEP-32496, GDC-0879, NMS-P186, NMS-P349, NMS-P383, NMS-P396, NMS-P730, PLX3603 (RO5212054), PLX4720 (Difluorophenyl-sulfonamine), PF-04880594, PLX4734, RAF265, RO4987655, SB590885, ZM336372, BMS908662, WYE-130600, TAK632, MLN 2480, XL281, a compound of formula (I):

(I)

wherein R is selected from the group consisting of p-chlorophenyl, 3-ethynylphenyl, 3-chloro-4-fluorophenyl, 2-fluoro-4-iodophenyl, 4-chloro-3-(trifluoromethyl) phenyl, 3-(1,1-dimethylethyl)-1-methyl-1H-pyrazol-5-yl, 3-(trifluoromethoxy)phenyl, 3,5-dihydroxyphenyl, phenyl-3-sulfonamide or 3-(trifluoromethyl)phenyl, or a pharmaceutically acceptable salt or a solvate thereof;

a compound of formula (II):

(II)

wherein R is NHR1, wherein R1 is 2-fluoro-4-iodophenyl, or a pharmaceutically acceptable salt or a solvate thereof;

a compound of formula (III):

(III)

wherein R is NHR1, wherein R1 is 3-ethynylphenyl, 3-chloro-4-fluorophenyl, 2-fluoro-4-iodophenyl, or 4-chloro-3-(trifluoromethyl) phenyl, or a pharmaceutically acceptable salt or a solvate thereof;

or a combination thereof; and a pharmaceutically acceptable carrier or excipient.

In some embodiments, there is provided the above use, wherein the BRaf inhibitor is the compound of formula (I) and wherein R is 3-(trifluoromethoxy)phenyl. In some embodiments, there is provided the use of any one of above embodiments, wherein the BRaf inhibitor inhibits the activity of BRaf and increases cell proliferation In some embodiments, there is provided the use of the topical composition of this disclosure comprising a therapeutically and/or prophylactically effective dose of at least one BRaf inhibitor or a combination thereof and a pharmaceutically acceptable carrier or excipient for the treatment, prevention or alleviation of radiation dermatitis by topical administration to a subject in need thereof, wherein said composition is formulated for topical administration.

In some embodiments, there is provided the above use, wherein the topical composition is in the form of a gel, a hydrogel, an ointment, a cream, a paste, a foam, a spray, a lotion, a liquid or a dermal patch.

In some embodiments, there is provided the use of any one of compositions of this disclosure, wherein the BRaf inhibitor in the composition is present at a concentration of 1% w/w to 5% w/w of the total weight of the composition, In some embodiments, there is provided the use of any one of compositions of this disclosure, wherein the BRaf inhibitor in the composition is present at a concentration of 0.1% w/w to 10% w/w of the total weight of the composition.

In some embodiments, there is provided the use of any one of compositions of this disclosure, wherein the use reduces the severity or prevents the escalation of the radiation dermatitis.

In some embodiments, there is provided the use of any one of compositions of this disclosure, wherein the use reduces the severity of the cutaneous adverse reaction from grade 4 to grade 3, 2, 1, or 0 as defined by National Cancer Institute Common Terminology Criteria for Adverse Events (NCI-CTCAE) version 5.0 or according to the Radiation Therapy Oncology Group (RTOG) grading scale.

In some embodiments, there is provided the use of any one of compositions of this disclosure, wherein the use reduces the severity of the cutaneous adverse reaction from grade 3 to grade 2, 1, or 0, as defined by National Cancer Institute Common Terminology Criteria for Adverse Events (NCI-CTCAE) version 5.0 or corresponding RTOG grades.

In some embodiments, there is provided the use of any one of compositions of this disclosure, wherein the use reduces the severity of the cutaneous adverse reaction from grade 2 to grade 1 or 0, as defined by National Cancer Institute Common Terminology Criteria for Adverse Events (NCI-CTCAE) version 5.0 or corresponding RTOG grades.

In some embodiments, there is provided the use of any one of compositions of this disclosure, wherein the use reduces the severity of the cutaneous adverse reaction from grade 1 to grade 0, as defined by National Cancer Institute Common Terminology Criteria for Adverse Events (NCI-CTCAE) version 5.0 or corresponding RTOG grades.

In some embodiments, there is provided the use of any one of compositions of this disclosure, wherein the use prevents the escalation of the cutaneous adverse reaction from grade 0 to grade 1, 2, 3, or 4, as defined by National Cancer Institute Common Terminology Criteria for Adverse Events (NCI-CTCAE) version 5.0 or corresponding RTOG grades.

In some embodiments, there is provided the use of any one of compositions of this disclosure, wherein the use prevents the escalation of the cutaneous adverse reaction from grade 1 to grade 2, 3, or 4, as defined by National Cancer Institute Common Terminology Criteria for Adverse Events (NCI-CTCAE) version 5.0 or corresponding RTOG grades.

In some embodiments, there is provided the use of any one of compositions of this disclosure, wherein the use prevents the escalation of the cutaneous adverse reaction from grade 2 to grade 3 or 4, as defined by National Cancer Institute Common Terminology Criteria for Adverse Events (NCI-CTCAE) version 5.0 or corresponding RTOG grades.

In some embodiments, there is provided the use of any one of compositions of this disclosure, wherein the use prevents the escalation of the cutaneous adverse reaction from grade 3 to grade 4, as defined by National Cancer Institute Common Terminology Criteria for Adverse Events (NCI-CTCAE) version 5.0 or corresponding RTOG grades.

EXAMPLES

Example 1

Effect of the Compounds—LUT012, LUT013, LUT014, LUT015, LUT016, LUT017, LUT-019, LUT020, C-1, and Vemurafenib—on Proliferation of MIA PaCa Cells In this example, effect of the compounds on proliferation of MIA PaCa2 K-ras cells was studied. It was expected that the compounds that induce ERK phosphorylation would also induce proliferation of Mia PaCa cells.

The cells were seeded in starvation medium at 5000 cells/well in a 96 wells plate for 24 hours at 37° C., 5% $CO_2$. The tested compounds were added at different concentrations ranging from 0.002 µM to 10 µM. The controls were untreated cells and vehicle of 0.1% DMSO. The cells were incubated at 37° C., 5% $CO_2$, for 72 hours and then the proliferation was tested using the ATPlite proliferation kit (Perkin-Elmer). Each result represents an average of 6 wells. The results are presented as the percent of over-proliferation compared to the DMSO control.

Figure 1:
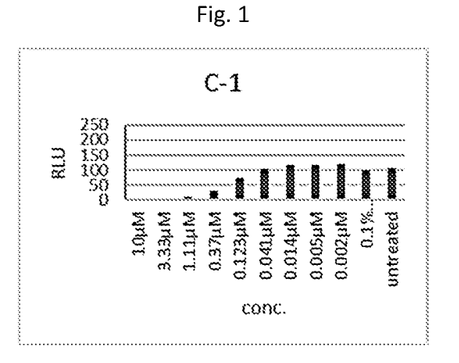
FIG. 1—depicts the effects of compound C-1 on proliferation of MIA PaCa cells.
Figure 2:
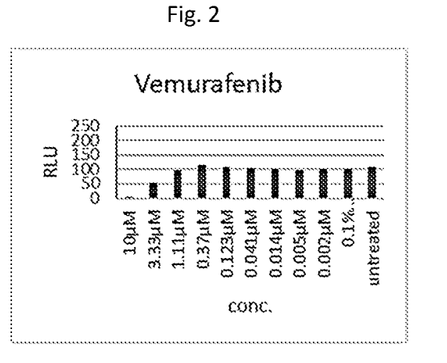
FIG. 2—depicts the effects of compound Vemurafenib on proliferation of MIA PaCa cells.
Figure 3:
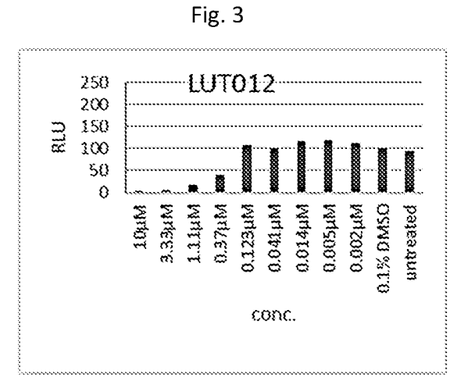
FIG. 3—depicts the effects of compound LUT-012 on proliferation of MIA PaCa cells.
Figure 4:
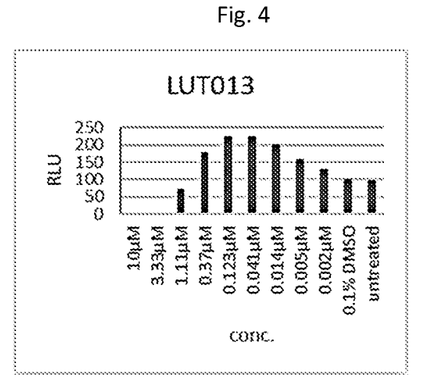
FIG. 4—depicts the effects of compound LUT-013 on proliferation of MIA PaCa cells.
Figure 5:
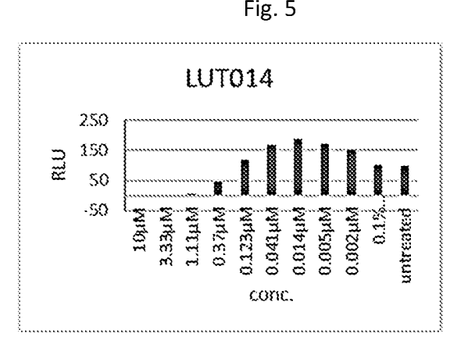
FIG. 5—depicts the effects of compound LUT-014 on proliferation of MIA PaCa cells.
Figure 6:
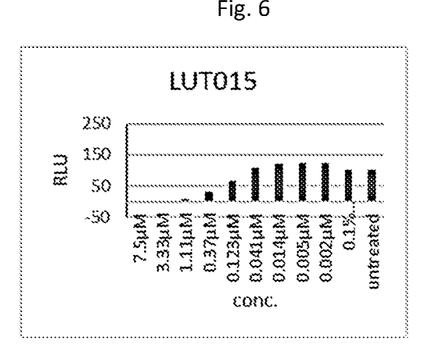
FIG. 6—depicts the effects of compound LUT-015 on proliferation of MIA PaCa cells.

The concentration of the compounds that provided the highest proliferation was compared to DMSO. DMSO was calculated as 100%. After 72 hours, % proliferation compared to the DMSO control induced by C-1 was 30%, LUT013 was 173%, LUT014 was 116%, LUT015 was 29%, LUT016 was 110%, LUT017 was 174%, LUT012 was 20%, LUT019 was 7%, and LUT020 was 12%. Vemurafenib showed 12% proliferation compared to DMSO (see FIG. 1-6).

What we claim is:

1. A method for treating, preventing or alleviating of radiation dermatitis, the method comprising:
    administering topically to a subject in need thereof a composition comprising a therapeutically or prophylactically effective dose of at least one BRaf inhibitor or a combination thereof and a pharmaceutically acceptable carrier or excipient,
    wherein the method reduces the severity or prevents the escalation of the radiation dermatitis.

2. The method of claim 1, wherein the at least one BRaf inhibitor comprises BAY43-9006 (Sorafenib), LGX818 (encorafenib), PLX4032 (vemurafenib), GSK2118436 (dabrafenib), ARQ736, ARQ680, AZ628, C-1, C-15, C-19, C-A, CEP-32496, GDC-0879, NMS-P186, NMS-P349, NMS-P383, NMS-P396, NMS-P730, PLX3603 (R05212054), PLX4720 (Difluorophenyl-sulfonamine), PF-04880594, PLX4734, RAF265, R04987655, SB590885, ZM336372, BMS908662, WYE-130600, TAK632, MLN 2480, XL281, a compound of formula (I):

wherein R is selected from the group consisting of p-chlorophenyl, 3-ethynylphenyl, 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, 3,5-dihydroxyphenyl, phenyl-3-sulfonamide or 3-(trifluoromethyl)phenyl, or a pharmaceutically acceptable salt or a solvate thereof;

a compound of formula (II):

wherein R is NHR1, wherein R1 is 2-fluoro-4-iodophenyl, or a pharmaceutically acceptable salt or a solvate thereof;

a compound of formula (III):

wherein R is NHR1, wherein R1 is 3-ethynylphenyl, 3-chloro-4-fluorophenyl, 2-fluoro-4-iodophenyl, or 4-chloro-3-(trifluoromethyl) phenyl, or a pharmaceutically acceptable salt or a solvate thereof.

3. The method of claim 2, wherein the at least one BRaf inhibitor is the compound of formula (I) and wherein R is 3-(trifluoromethoxy)phenyl.

4. The method of claim 1, wherein administration of the at least one BRaf inhibitor inhibits the activity of BRaf and increases cell proliferation.

5. The method of claim 1, wherein the composition is in the form of a gel, a hydrogel, an ointment, a cream, a paste, a foam, a spray, a lotion, a liquid or a dermal patch.

6. The method of claim 1, wherein the composition comprises the at least one BRaf inhibitor at a concentration of 1% w/w to 5% w/w of the total weight of the composition.

7. The method of claim 1, wherein the composition comprises the at least one BRaf inhibitor at a concentration of 0.1% w/w to 10% w/w of the total weight of the composition.

8. The method of claim 1, wherein the method reduces the severity of the cutaneous adverse reaction from grade 4 to grade 3, 2, 1, or 0 as defined by National Cancer Institute Common Terminology Criteria for Adverse Events (NCI-CTCAE) version 5.0 or according to the Radiation Therapy Oncology Group (RTOG) grading scale.

9. The method of claim 1, wherein the method reduces the severity of the cutaneous adverse reaction from grade 3 to grade 2, 1, or 0, as defined by National Cancer Institute Common Terminology Criteria for Adverse Events (NCI-CTCAE) version 5.0 or corresponding RTOG grades.

10. The method of claim 1, wherein the method reduces the severity of the cutaneous adverse reaction from grade 2 to grade 1 or 0, as defined by National Cancer Institute Common Terminology Criteria for Adverse Events (NCI-CTCAE) version 5.0 or corresponding RTOG grades.

11. The method of claim 1, wherein the method reduces the severity of the cutaneous adverse reaction from grade 1 to grade 0, as defined by National Cancer Institute Common Terminology Criteria for Adverse Events (NCI-CTCAE) version 5.0 or corresponding RTOG grades.

12. The method of claim 1, wherein the method prevents the escalation of the cutaneous adverse reaction from grade 0 to grade 1, 2, 3, or 4, as defined by National Cancer Institute Common Terminology Criteria for Adverse Events (NCI-CTCAE) version 5.0 or corresponding RTOG grades.

13. The method of claim 1, wherein the method prevents the escalation of the cutaneous adverse reaction from grade 1 to grade 2, 3, or 4, as defined by National Cancer Institute Common Terminology Criteria for Adverse Events (NCI-CTCAE) version 5.0 or corresponding RTOG grades.

14. The method of claim 1, wherein the method prevents the escalation of the cutaneous adverse reaction from grade 2 to grade 3 or 4, as defined by National Cancer Institute Common Terminology Criteria for Adverse Events (NCI-CTCAE) version 5.0 or corresponding RTOG grades.

15. The method of claim 1, wherein the method prevents the escalation of the cutaneous adverse reaction from grade 3 to grade 4, as defined by National Cancer Institute Common Terminology Criteria for Adverse Events (NCI-CTCAE) version 5.0 or corresponding RTOG grades.

16. The method of claim 3, wherein topical administration of the compound of formula (I) wherein R is 3-(trifluoromethoxy)phenyl inhibits the activity of BRaf and increases cell proliferation.

17. The method of claim 3, wherein the composition comprises the compound of formula (I) wherein R is 3-(trifluoromethoxy)phenyl at a concentration of 1% w/w to 5% w/w of the total weight of the composition.

18. The method of claim 3, wherein the composition comprises the compound of formula (I) wherein R is 3-(trifluoromethoxy)phenyl at a concentration of 0.1% w/w to 10% w/w of the total weight of the composition.

* * * * *